United States Patent
Morris (10) Patent No.: US 6,664,246 B2
(45) Date of Patent: Dec. 16, 2003

(54) PHARMACEUTICAL COMPOSITION

(75) Inventor: David Morris, Lugarno (AU)

(73) Assignee: MRC Holdings PTY Limited, Sydney (AU)

( * ) Notice: Subject to any disclaimer, the term of this patent is extended or adjusted under 35 U.S.C. 154(b) by 0 days.

(21) Appl. No.: 09/861,865

(22) Filed: May 22, 2001

(65) Prior Publication Data

US 2002/0128239 A1 Sep. 12, 2002

Related U.S. Application Data

(63) Continuation of application No. 09/674,750, filed as application No. PCT/AU99/00323 on May 4, 1999, now abandoned.

(51) Int. Cl.[7] .......................... A61K 31/59; A61K 31/20
(52) U.S. Cl. ........................................ 514/167; 514/560
(58) Field of Search .................................. 514/167, 560

(56) References Cited

U.S. PATENT DOCUMENTS 5,486,509 A * 1/1996 Jimenez et al. .............. 514/167

FOREIGN PATENT DOCUMENTS

EP 0 619 305 A1 10/1994
EP 0 970 948 A1 1/2000

OTHER PUBLICATIONS

Ayoub et al. "Tamoxifen–induced female androgenetic alopecia in a patient with breast cancer" Annuls of Internal Medicine (USA), May 1, 1997 vol. 126, pp. 745–746. ISSN: 0003–4819. ISSN: 0003–4819.*

Finlay, et al.; "The Use of Lipiodol and Medium Chain Triglyceride as Delivery Agents for Heptac Arterial Administration of 1,25–Dihydroxyvitamin $D_3$—A Potential New Treatment for Hepatocelular Carcinoma"; Anticancer Research; 20: 2705–2710 (2000); XP001079260.

* cited by examiner

*Primary Examiner*—Theodore J. Criares
*Assistant Examiner*—Jennifer Kim
(74) *Attorney, Agent, or Firm*—Nixon & Vanderhye (57) ABSTRACT

The present invention is concerned with a pharmaceutical composition suitable for the treatment of cancer and in particular with a pharmaceutical composition containing vitamin D or a precursor, analogue or metabolite thereof and the use of these compositions in the treatment of a tumor in a subject.

15 Claims, 12 Drawing Sheets

Effect of chronic vitamin D treatment on cell count

PHARMACEUTICAL COMPOSITION

This Application is a continuation of U.S. application Ser. No. 09/674,750, now abandoned which is a 371 of PCT/AU99/00323 filed May 4, 1999.

BACKGROUND OF THE INVENTION

The present invention is concerned with pharmaceutical compositions suitable for the treatment of cancer, and in particular, with pharmaceutical compositions containing vitamin D or a precursor, analogue or metabolite thereof and the use of these compositions in the treatment of a tumor in a subject.

Vitamin D is an isoprenoid compound made up of activated 5-carbon units. The most abundant form of vitamin D is vitamin $D_3$, or cholecalciferol. Vitamin $D_3$ arises from biosynthesis of 7-dehydrocholesterol, an intermediate in cholesterol biosynthesis. Vitamin $D_3$ is metabolised in the liver to 25-hydroxycholecalciferol [$25(OH)D_3$] which is a major form of Vitamin D circulating in the blood compartment $25(OH)D_3$ is converted by the kidney to produce two principal dihydroxylated metabolites, namely, 1,25-dihydroxycholecalciferol [$1,25(OH)_2D_3$] and 24,25-dihydroxycholecalciferol [$24R,25(OH)_2D_3$].

$1,25(OH)_2D_3$ is the most biologically active naturally occurring form of vitamin $D_3$ and is transported in the bloodstream to its major site of action in the mucosal cells of the intestine, where calcium absorption is stimulated. Thus vitamin $D_3$ may be regarded as a prohormone because it is converted to a metabolite that acts analogously to a steroid hormone. It regulates calcium and phosphorous metabolism particularly in the synthesis of the inorganic matrix of bones.

Systemic administration of high doses of vitamin $D_3$ or its metabolites is limited by the production of hypercalcaemia. This has led to the development of analogues of activated vitamin D ($D_3$) which have a greater effect on cell growth than on calcium metabolism. These compounds have been found to be effective in the inhibition of growth of breast, rectal, colorectal and prostate cancer cells.

DISCLOSURE OF THE INVENTION

We have found that tumors in certain organs, for example, primary and secondary tumors in the liver, can be treated by regional delivery of high concentrations of $1,25(OH)_2D_3$ to the affected organ without giving rise to hypercalcaemia. Applicant's co-pending International Application No. PCT/AU98/00440, the disclosure of which is incorporated herein by reference, discloses a method for the treatment of liver cancer by means of regional delivery of vitamin D or its metabolite or analogues to the liver.

The effect on tumors is very dose dependent and there is therefore advantage in delivering higher concentrations of vitamin D compounds such as $1,25(OH)_2D_3$. However, the limited solubility of vitamin D and its precursors, analogues and metabolites in a conventional carrier such as water places an upper limit on the concentration of the compound that can be delivered to the organ. Delivery of vitamin $D_3$ intra-arterially in a conventional carrier limits the vitamin $D_3$ concentration in the blood going to the liver to at most $10^{-7}$ mole per liter.

We have found that very high concentrations of vitamin D compound such as $1,25(OH)_2D_3$ can be achieved by dissolving $1,25(OH)_2D_3$ in a lipid, for example, an iodised or non-iodised oil. A further advantage of using an oil as the carrier for the vitamin D compound is that some oils are concentrated in certain cancers allowing the achievement of very high tumor concentrations of vitamin $D_3$. Moreover, we believe that the use of a lipid as the carrier for the vitamin D compound results in a sustained antiproliferative activity of the vitamin D compound and the compound is retained for considerably longer periods within the tumor.

Accordingly, in a first aspect, the present invention provides a pharmaceutical composition suitable for use in the treatment of cancer cells in an organ by regional delivery of the composition to the organ, the composition including a vitamin D compound and a pharmaceutically acceptable lipid, wherein the concentration of the vitamin D compound in the composition is greater than about $1\times10^{-7}$ mole per liter.

By the term "vitamin D compound" we include the biologically active and inactive forms of vitamin D. The vitamin D compound may be a precursor, metabolite or analogue of vitamin D. The vitamin D compound may be any analogue having anti-tumor properties. The vitamin D compound maybe cholecalciferol, $25(OH)D_3$ or $1,25(OH)_2D_3$. Examples of analogues of vitamin D include, but are not restricted to, EB1089, OCT (22-oxa-1,25(OH)$_2D_3$), $1\alpha25(OH)_2$, 22,24 diene, 24, 26, 27 trihomo $D_3$, MC903 (calcipotriol) and KH1060, $1,25(OH)_2$-16-ene 23-yne vitamin $D_2$ and its hexadeutero form. The vitamin D compound may be vitamin $D_5$ or an analogue thereof.

Preferably the concentration of vitamin D compound in the composition of the invention is at least about $1\times10^{-6}$ mole per liter. The concentration of vitamin D compound may be at least about $1\times10^{-5}$ mole per liter. The concentration may be at least about $1\times10^{-4}$ mole per liter. The concentration may be at least $1\times10^{-}$ mole per liter. A preferred concentration of the vitamin D compound is about $1\times10^{-6}$ to $50\times10^{-5}$ mole per liter.

Preferably the lipid used is one for which the tumor is avid so that high concentrations of the vitamin D compound are delivered to the tumor. To determine whether the tumor being treated is lipid avid or not a-small dose of lipid may be given into the hepatic artery by a percutaneous or surgically placed catheter. A tumor that is not lipid avid is unlikely to benefit from the treatment to the same extent as a tumor that is avid to the the lipid used.

The pharmaceutically acceptable lipid may be an oil. A non-iodised oil is preferred. The non-iodised oil may be any pharmaceutically acceptable oil in which the vitamin D compound is soluble. The non-iodised oil may be a vegetable oil. The oil may be, for example, poppy seed oil, soybean oil, sesame oil, safflower oil, peanut oil, cremophore, Liposyn or Intralipid. The oil may be derived from shark liver oil including squalane and squalene. The lipid may be medium chain triglycerides (MCT).

An iodised oil such as iodised poppy seed oil (lipiodol) can be used, however, the iodine has the effect of making the vitamin D compound more light sensitive.

The lipid may be in the form of an emulsion of these oils prepared with pharmaceutically acceptable emulsifying agents including, but not limited to, natural and synthetic phospholipids, Spans, Tweens or Pluronics, We have found that very high concentrations of activated vitamin $D_3$ in lipiodol can be achieved. For example, 2 mg of $1,25(OH)_2$ $D_3$ can be readily dissolved in one ml of iodised poppy seed oil.

Apart from providing a composition that is more effective in the treatment of tumors, the higher concentrations of vitamin D compounds achievable in the composition of the invention provide a reservoir of the vitamin D compound, which is released over time, thus allowing for "one shot" administration of the composition.

Furthermore, because the composition of the invention is capable of providing higher concentrations of vitamin D, even non-active forms of vitamin D may be used to treat tumors. Although at low concentrations these non-active forms may not be effective treating tumors, at very high concentrations they may become effective.

The composition of the invention may further include one or more other components. The present composition may contain a component that is capable of increasing vitamin D receptor expression. The composition may include an estrogen, estrogen-like compound or estrogen antagonist. The component may be tamoxifen.

The composition may be used to treat primary or secondary tumors in any organ to which the composition can be administered by regional delivery.

Accordingly, the present invention further extends to a method for the treatment of a tumor in an organ in a subject, the method including regional administration to the organ of a composition in accordance with the present invention.

The regional delivery, may be by means of intra-arterial delivery, for example, by intra-arterial infusion. Alternatively, the composition of the invention may be delivered to the portal vein. The tumor may be a primary or secondary tumor. The organ treated may be the liver, breast, prostate, bone tumor or kidney. The composition of the invention may also be used to treat colorectal cancer or sarcomas. The method and composition of the present invention are particularly suitable for the treatment of hepatoma.

The vitamin D compound may be dissolved in lipid as described above, for example, iodised or non-iodised poppy seed oil to the desired concentration of vitamin D compound.

The method of the invention may be repeated at monthly, or other, intervals. It will be readily apparent that the composition and method of the present invention provide the capability of delivering very high local concentration of vitamin D substance delivered by the composition of the present invention will achieve tumor control and whilst avoiding hypercalcaemia.

In order to more fully describe the invention we provide the following non-limiting examples.

Modes for Carrying Out the Invention

1 Cell Culture Studies 1.1 Materials and Methods 1.1.1 Uptake Studies

For the uptake studies, monolayers of HepG2 cells were grown on sterile microscope cover glass, placed in 6 well tissue culture plates. Cells were exposed (24 h) to culture media (MEM-5% FBS) containing 1% lipiodol and stained by an oil-red O impregnation technique. This briefly involved fixation of the cells by 10% formalin followed by staining, differentiating and counter staining. Cells were thoroughly washed with phosphate buffer solution (pH 7.4), and water through out the fixation procedure. After fixation, cells were viewed and photographed under the microscope.

1.1.2 Cell Proliferation Assays

Following exposure of cells to vitamin $D_3$ dissolved in normal or lipiodol (1% v/v) containing media. [$^3$H] thymidine incorporation assay and the trypan blue exclusion cell count methods were used to determine cell proliferation. To do this, cells were plated in 24 well tissue culture plates at $10^4$ cells per well and incubated for 24 h in an incubator at 37° C. with humidified 5% $CO_2$ atmosphere. The, medium was replaced with one containing vitamin $D_3(10^{-11}$ to $10^{-7}$ M) dissolved in either the normal medium or first dissolved in lipiodol and then mixed thoroughly with the medium to make a final lipiodol concentration of 1% (v/v). For acute dose studies, cells were exposed to one of the two drug containing media for 24 h, which were then replaced with drug free medium for the next four days. Whilst, in chronic treatment, cells were exposed for 5 days to different concentrations of the drug dissolved in one of the media described above. The media were changed on alternate days.

At the end of treatment period, cell cultures were assayed for thymidine incorporation by the addition of 0.1µ Ci of [$^3$H]thymidine to each well for the last 4 h of culture. The amount of radioactivity incorporated into trichloroacetic acid precipitatable material was determined using a β-scintillation counter. Results are plotted as percentage inhibition relative to control. The control cells for the vitamin $D_3$/lipiodol group were treated with a lipiodol-containing medium (1%).

For the cell count assay, cells were plated in six well plates at a concentration of $5 \times 10^4$ cells per well. Cell treatment procedure was a described for the thymidine assay. At the end of the treatment period (5 days), cells were trypsinised and counted with a hemocytometer. All counts were obtained in quadruplicate and each experiment was repeated at least twice. Unpaired Students t-test was used for comparisons of treated versus control values and p<0.05 was considered to represent a significant difference.

1.2 Results

Figure 1:
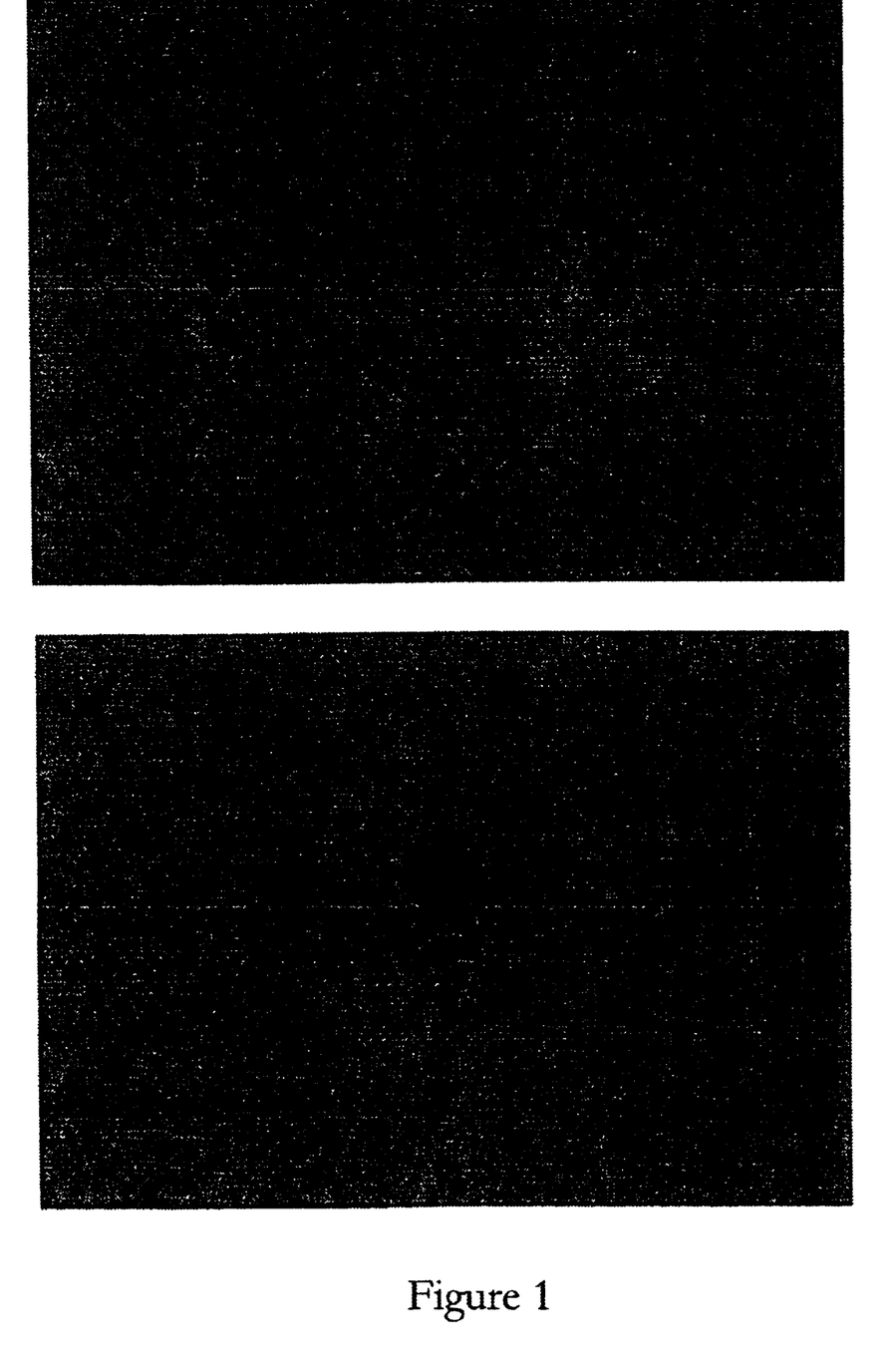
FIG. 1 is a photograph taken under a microscope showing uptake of lipiodol by HepG2 cells exposed to a medium with 1% lipiodol or without lipiodol (control). Lipiodol is stained red using the Oil red O technique.

HepG2 cells exposed to lipiodol consistently demonstrated multiple intracellular red vesicles of lipiodol on oil-red O impregnation, while, there was no sign of lipiodol in control cells (FIG. 1).

Figure 2:
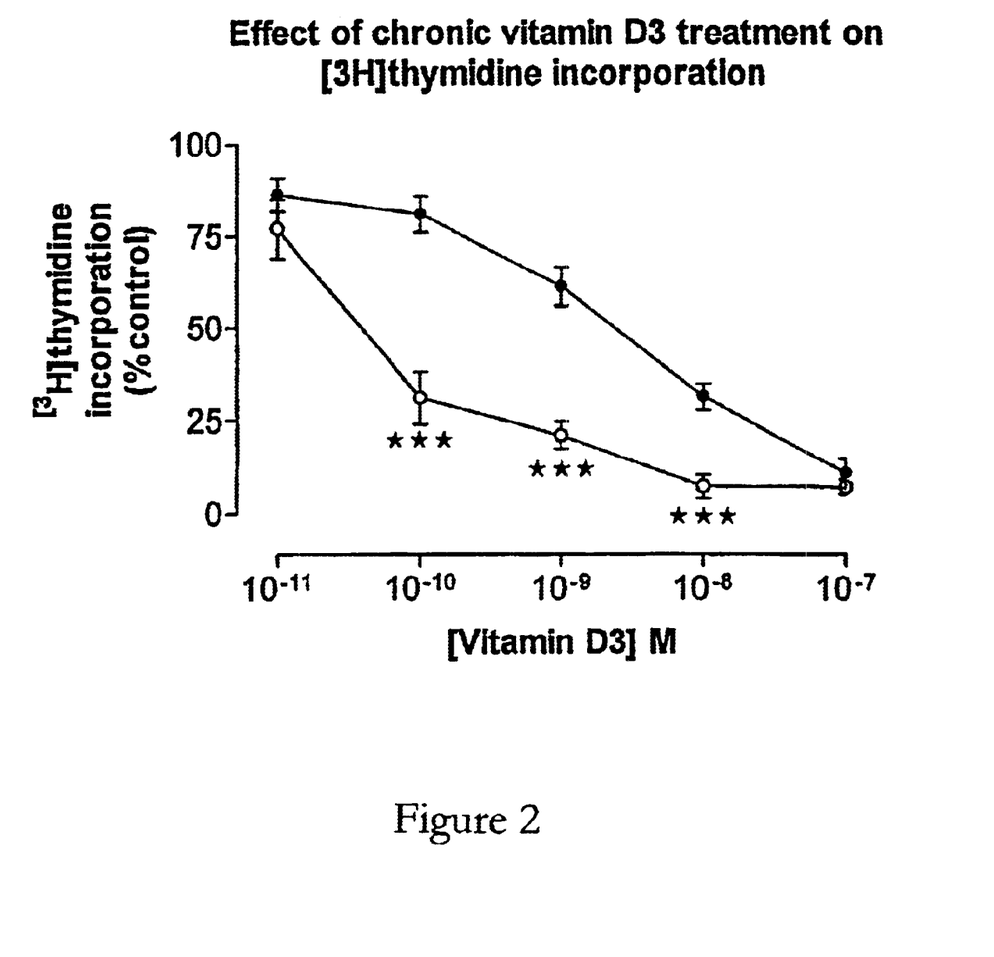
FIG. 2 is a graph showing [$^3$H]thymidine incorporation in HepG2 cells after 5 days treatment with different doses of vitamin $D_3$ in normal medium (—●—) or in 1% lipiodol (—○—). Values represent mean∓s.e.m. (***=$p<0.001$ using unpaired t-test).

When treated chronically, HepG2 cells showed significant reduction in thymidine incorporation at all concentrations of vitamin $D_3$ and in both delivery systems used. However, in cells exposed to the vitamin $D_3$/lipiodol delivery system, the degree of inhibition of thymidine incorporation was significantly greater (FIG. 2).

Figure 3:
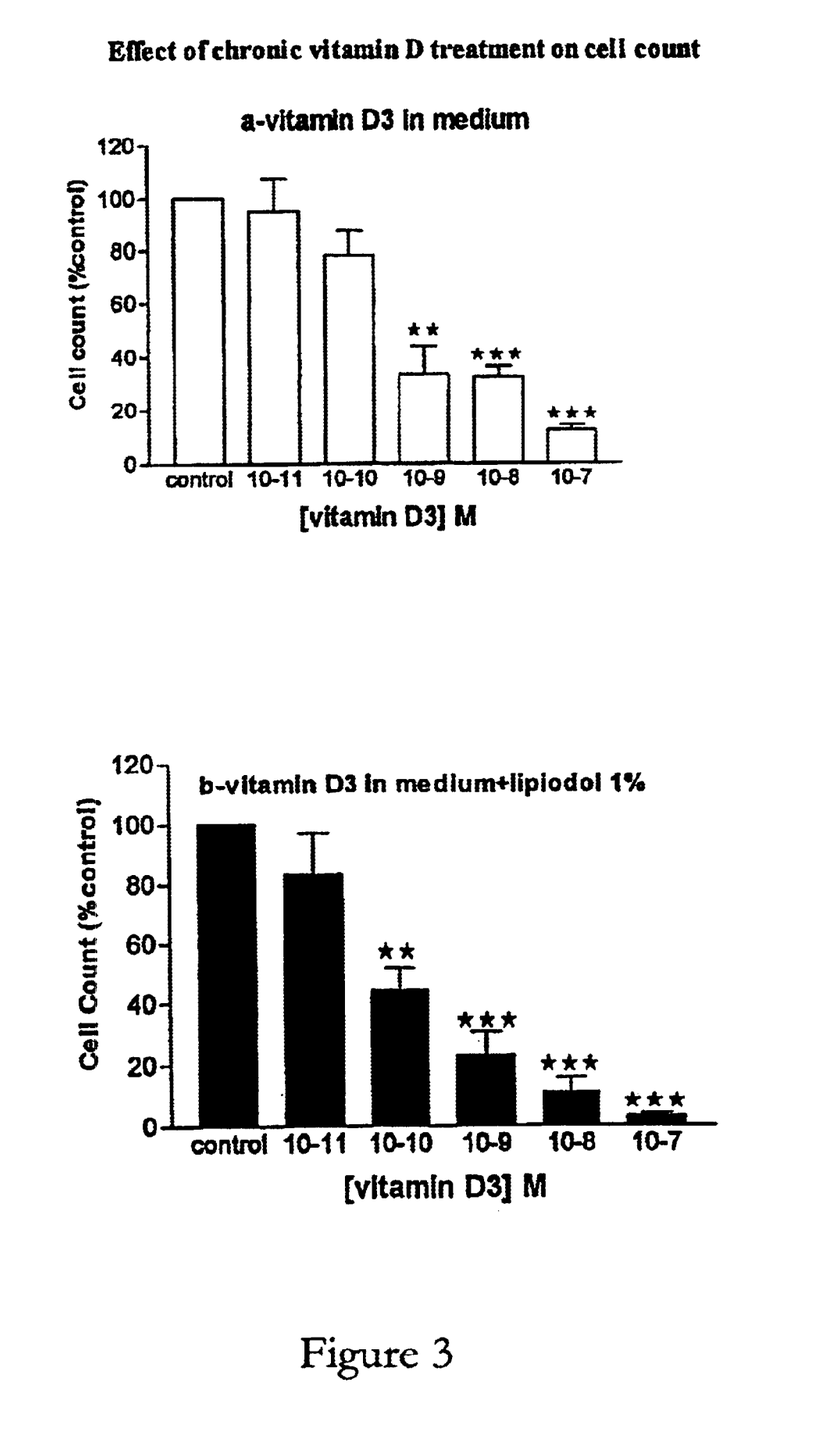
FIG. 3 provides bar graphs depicting cell counts per well (% of control) after HepG2 cells were exposed to vitamin $D_3$ for 5 days with different doses of vitamin $D_3$ dissolved in normal medium (a) or in 1% lipiodol (b). Values represent mean∓s.e.m. (***=$p<0.001$ using unpaired t-test).
Figure 4:
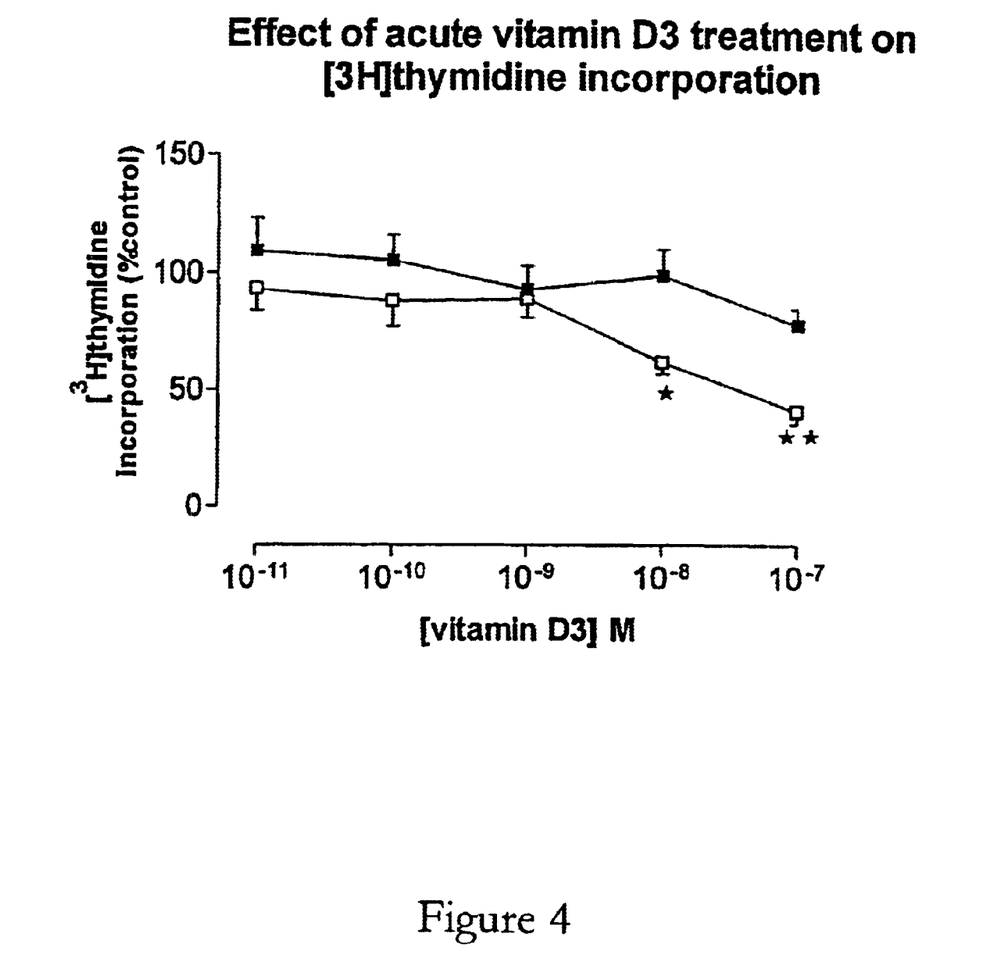
FIG. 4 provides graphs showing [$^3$H]thymidine incorporation in HepG2 cells after one day exposure to different doses of vitamin $D_3$ in normal medium (—■—) or in 1% lipiodol (—□—), followed by 4 days exposure to medium without the drug Values represent mean∓s.e.m. (***=$p<0.001$ using unpaired t-test.
Figure 5:
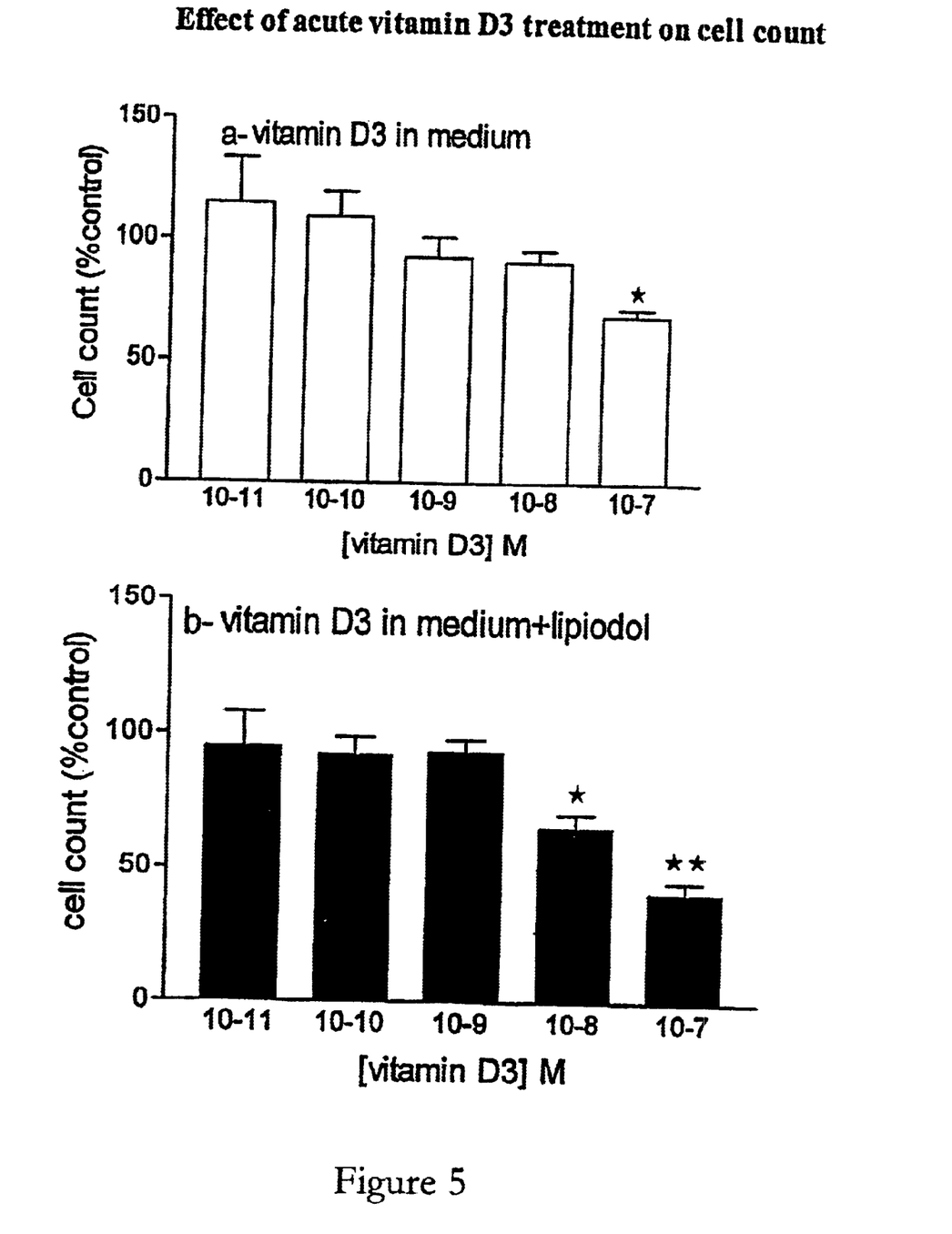
FIG. 5 provides bar graphs showing cell counts per well (% control) after HepG2 cells were exposed for 1 day to different doses of vitamin $D_3$ dissolved in normal medium (a) or in 1% lipiodol (b), followed by 4 days exposure to medium without the drug, values represent mean∓s.e.m. (***=$p<0.001$ using unpaired t-test).
Figure 6:
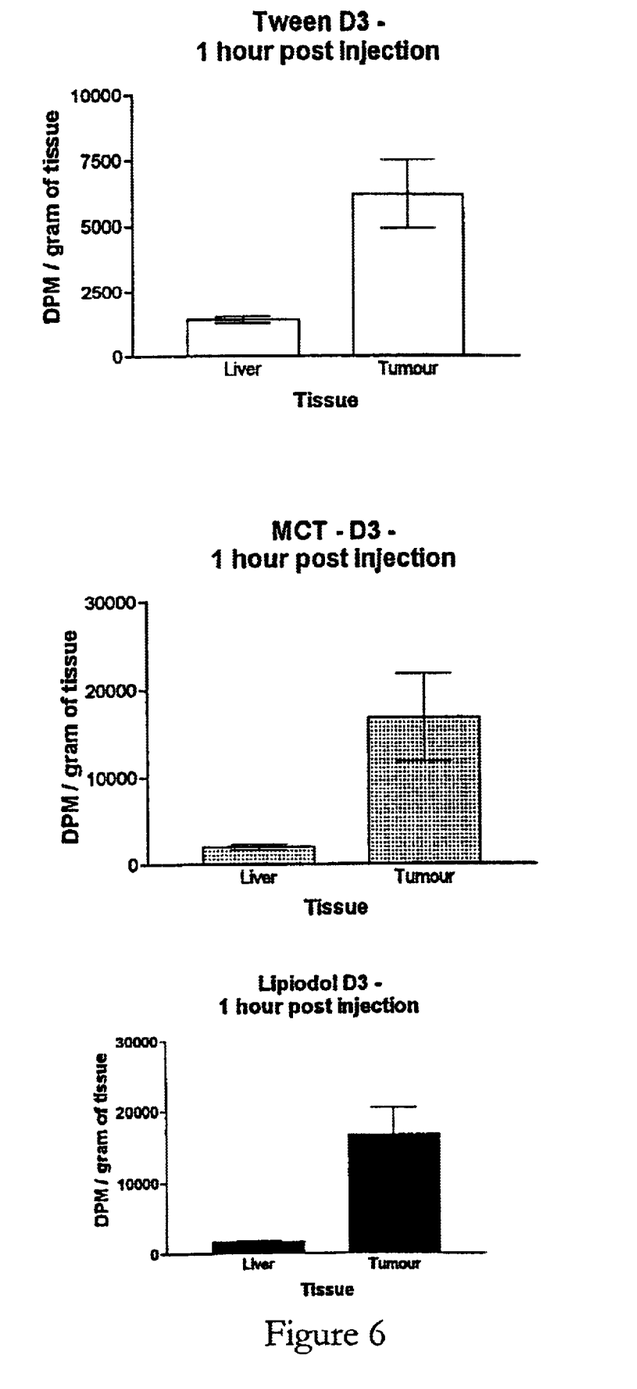
FIG. 6 provides bar graphs showing the 1 hour post injection level of radioactive vitamin $D_3$ in the liver, tumor and plasma of Sprague-Dawley rats following administration of vitamin $D_3$/Tween, vitamin $D_3$/MCT and vitamin $D_3$/lipiodol respectively as described in paragraph 2 below (In vivo studies in tumor bearing rats).
Figure 7:
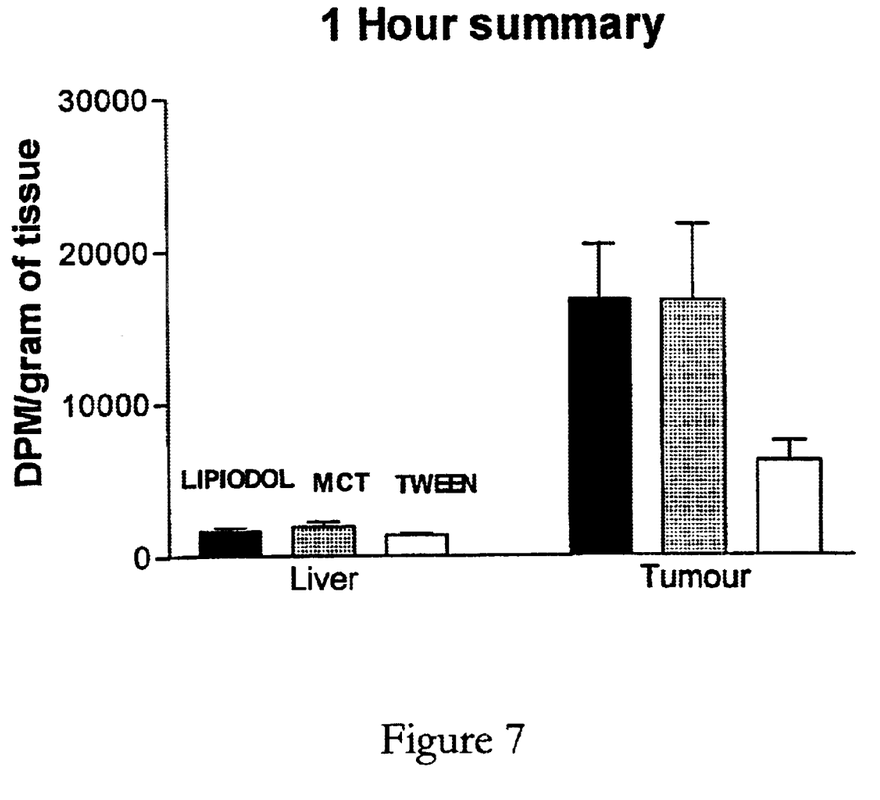
FIG. 7 is a bar graph giving a summary of the 1 hour results shown in FIG. 6.
Figure 8:
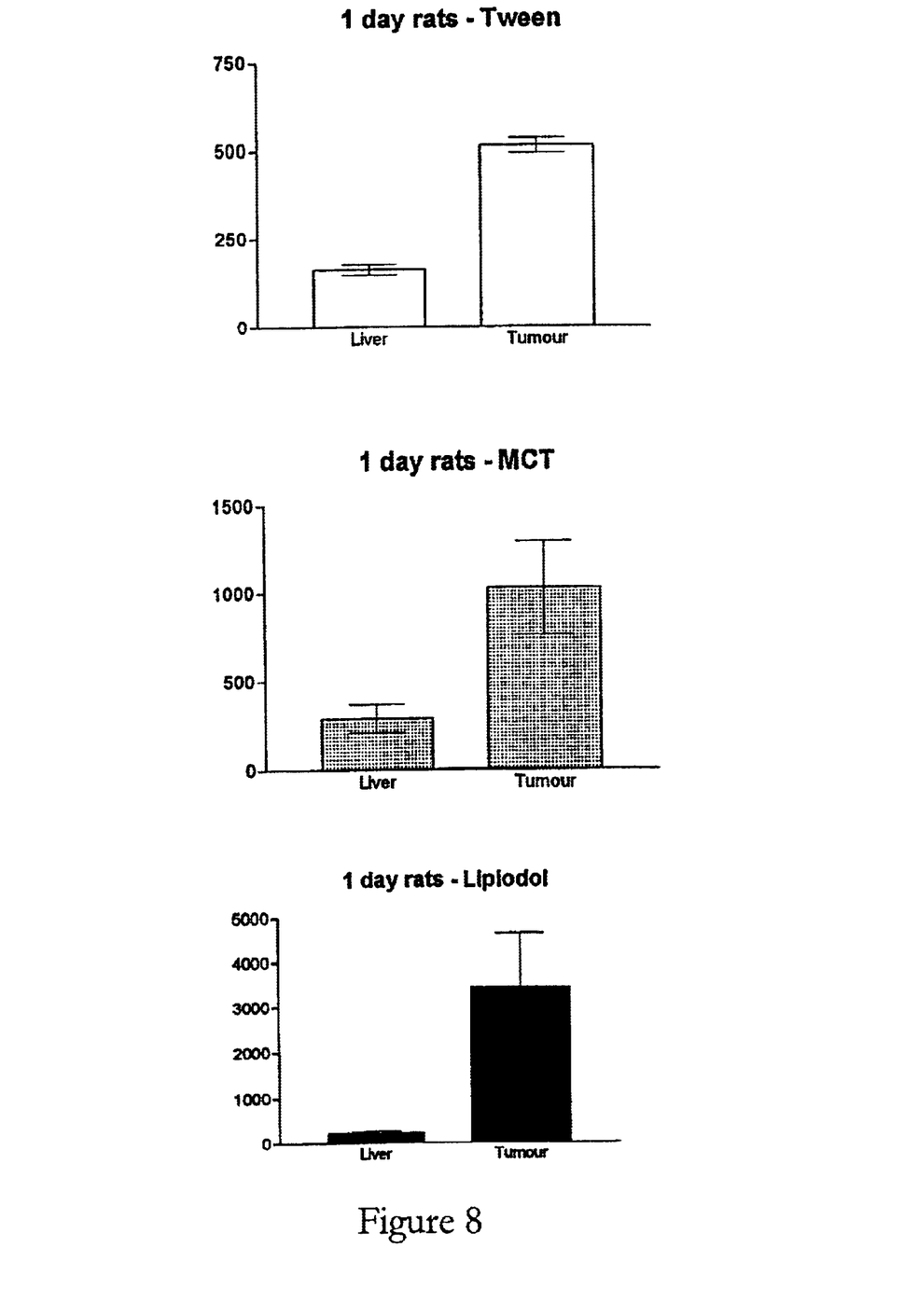
FIG. 8 provides bar graphs showing the 1 day post injection level of radioactive vitamin $D_3$ in the liver, tumor and plasma of Sprague-Dawley rats following of vitamin $D_3$/Tween, vitamin $D_3$/MCT and vitamin $D_3$/lipiodol respectively as described in paragraph 2.
Figure 9:
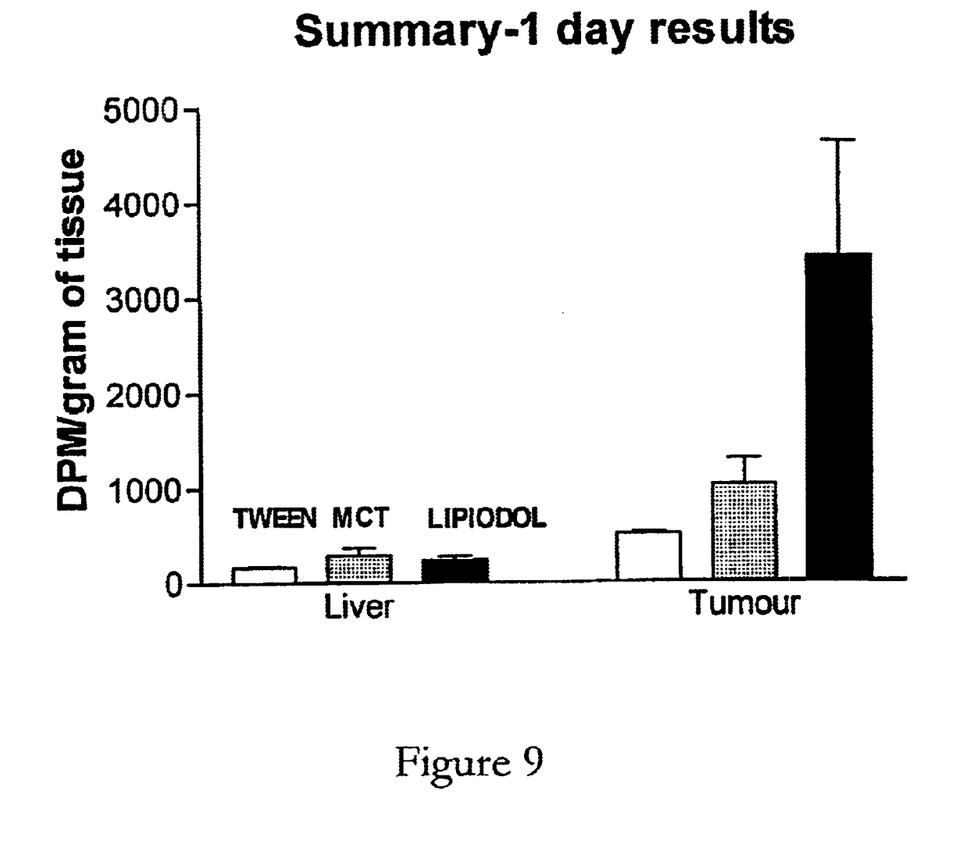
FIG. 9 is a bar graph giving a summary of the 1 day results shown in FIG. 8.
Figure 10:
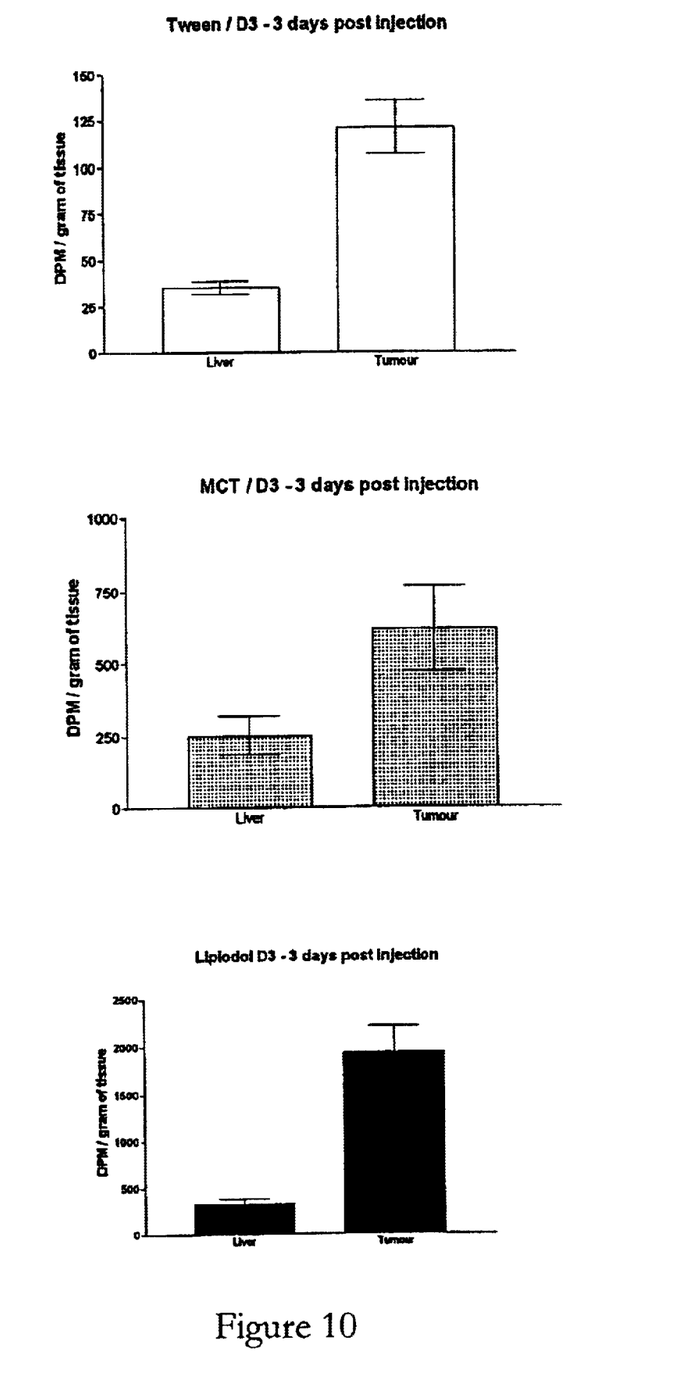
FIG. 10 provides bar graphs showing the 3 day post injection level of radioactive vitamin $D_3$ in the liver tumor and plasma of Sprague-Dawley rats following administration of vitamin $D_3$/Tween, vitamin $D_3$/MCT and vitamin $D_3$/lipiodol respectively as described in paragraph 2.
Figure 11:
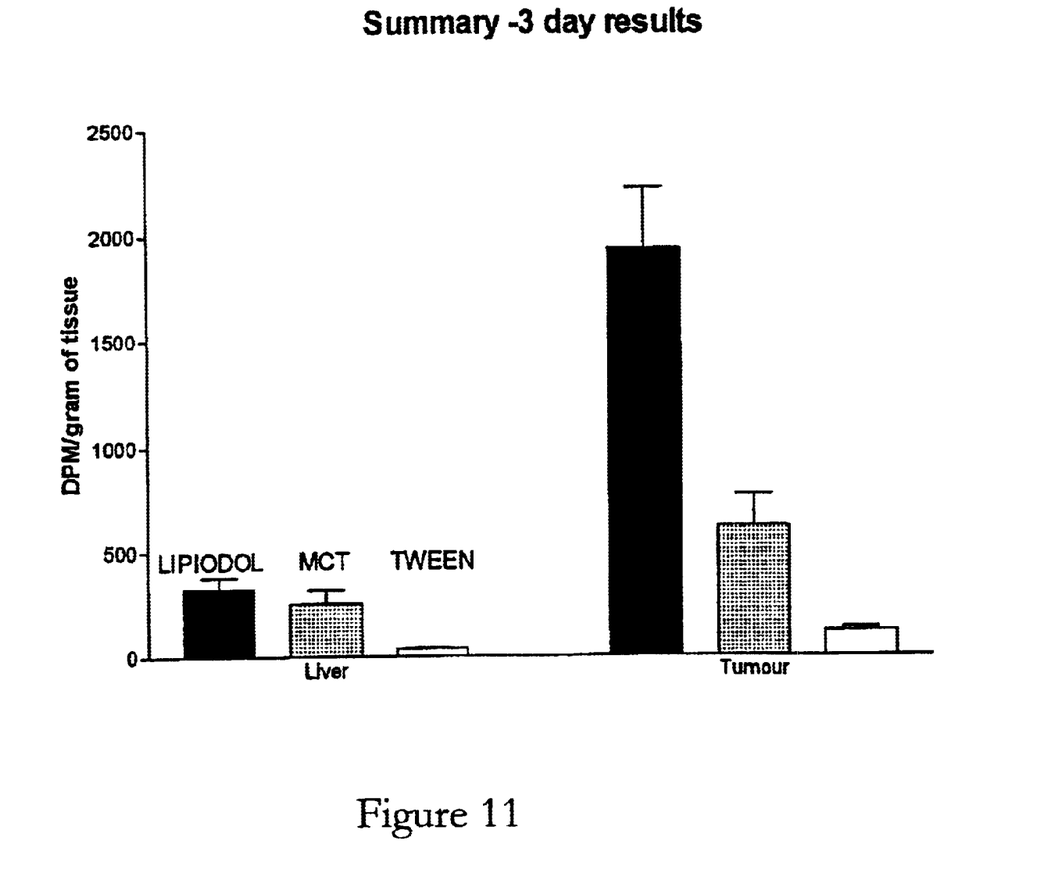
FIG. 11 is a bar graph giving a summary of the 3 day results shown in FIG. 10.

Similarly, upon chronic treatment of cells with either of the test media, cell proliferation was inhibited resulting in a dose dependant decrease in call number (FIG. 3). In acute studies, where cells were only exposed to the medium containing the drug for 1 day and to the medium without the drug for a further 4 days, compared to control, cells treated with vitamin $D_3$ made up in the medium alone, did not show a reduction in thymidine incorporation while those exposed to vitamin $D_3$ in lipiodol, showed significant reductions in thymidine incorporation (FIG. 4). In the cell count method, a significant reduction in cell number was observed in wells exposed to the $10^{-7}$ M concentration of vitamin $D_3$, while the vitamin $D_3$ lipiodol treated plates, wells exposed to $10^{-9}$, $10^{-8}$ and $10^{-7}$ M all showed significant reductions in the number of cells available within the wells (FIG. 5).

Note

1. The experiments described above were all also repeated using 1% MCT instead of 1% lipiodol in an exactly similar manner. The results obtained for MCT too, are also very similar to those of lipiodol showing significantly greater inhibition of proliferation in cells exposed to vitamin D3/MCT compared to those exposed to vitamin D3/medium.

2. In order to find an appropriate cell line, which would grow in the rat tumor and also be responsive to vitamin D3, rat cell lines, Novikoff and HTC were screened for responsiveness to vitamin D3($10^{-11}$–$10^{-6}$ M). Results obtained show that, Novikoff is a non responsive cell line to vitamin D3, while with HTC, an approximately 50% inhibition of proliferation was achieved with the $10^{-6}$ M concentration of the drug.

2. In Vivo Studies in Tumor Bearing Rats 2.1 Materials and Methods

Male 300–350 gr. Sprague-Dawely rats were given a general anaesthetic (halothane) and a lapratomy performed. Then $5 \times 10^6$ Novikoff cells suspended in 100 µl of medium was instilled beneath the liver capsule using a 26G3/8-tuberculin needle. The abdominal incision was then closed with gut suture.

All procedures were carried out under general anaesthesia and before reversing anaesthesia, animals were given a subcutaneous injection of the lipiodol analgesic buprenorphine (0.025 mg/kg).

Animals were then left for 10 days with food and water available ad libitum and monitored daily to assess health and well being. After this period, animals were randomly allocated to one of the treatment groups (n=6 per group) and lapratomy was performed again. A catheter was inserted into the hepatic artery of the animal, through which radiolabelled vitamin $D_3$ or vehicle injections were carried out. The different experimental groups treated were as follows:

Groups 1–3: receiving 100 µl of lipiodol

Groups 4–5: receiving vitamin D3 (hot+cold) in 100 µl of lipiodol

Groups 7–9: receiving 100 µl of MCT

Groups 10–12: receiving vitamin D3 (hot+cold) in 100 µl of MCT

Groups 13–15: receiving 100 µl of Tween

Groups 16–18: receiving vitamin D3 (hot+cold) in 100 µl of Tween

After administration of the drug, the catheter was removed and the incision sutured. Animals were euthanased at 1 hour, 1, and 3 days post drug (or vehicle) administration. Just before euthanasing, 3 ml of blood was drawn through cardiac puncture from each animal.

Post mortem, the liver and the tumor of each animal was excised, weighed and frozen in the freezer until analysis. After tissue homogenization, liver, tumor or plasma was extracted with dichloromethane. The amount of hot vitamin D3 present in each sample was determined using a β-counter.

2.2 Results

Results obtained are presented in FIGS. 6–11. From these results it can be seen that at 1 hour the level of radioactivity is high in all three samples of liver, tumor and plasma. While, in the 1 and 3 day samples the difference between tumor and those of liver and plasma is very different with much higher levels being available in the tumor for both lipiodol and MCT. Summary of the results for each time point (FIGS. 7, 9 and 11) clearly shows that in each case the level of radioactivity (vitamin D or metabolites) was greater in lipiodol treated animals. This in fact is a confirmation of the results obtained in the in vitro studies, showing that vitamin $D_3$ dissolved in lipiodol or MCT is taken up, retained and eventually released within the tumor. While, vitamin $D_3$ dissolved in a normal vehicle like Tween is rapidly cleared from the tumor and the body.

3. Human Studies: Phase 1 Clinical Trial 3.1 Patient Treatment

Patients suffering from primary HCC were selected according to the inclusion/exclusion criteria. After conduction of all medical and paramedical tests patients received a single dose of 50 µg vitamin $D_3$ dissolved in 5 ml of lipiodol through the hepatic artery administered by an expert radiologist Drug formulation was carried out under complete aseptic conditions in the oncology pharmacy unit of the hospital. Every 24 hours post drug administration, blood samples were withdrawn for the determination of serum AFP, calcium and vitamin $D_3$ levels daily for 3 days after which the patient was discharged from the hospital and visited once a week for 4 weeks (in total after drug administration).

3.2 Results

Figure 12:
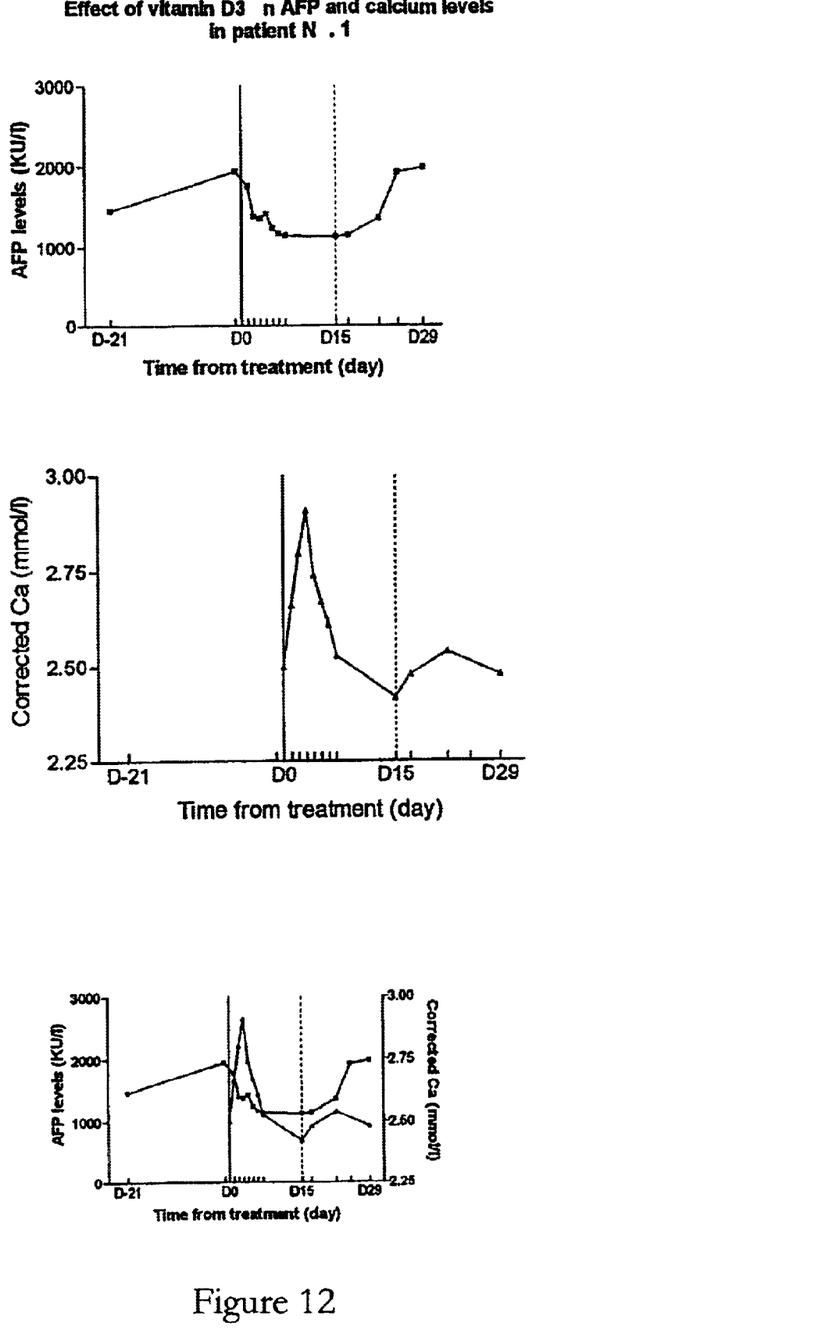
FIG. 12 provides graphs showing the effect of intra-hepatic arterial administration of vitamin $D_3$ (50 $\mu$g) on AFP and calcium levels in a patient with HCC.

Results obtained for AFP and calcium levels in the one patient who has completed the treatment so far are presented in FIG. 12.

It can be seen that the AFP levels dropped significantly, reached the lowest level around day 7 and remained low till day 15 after which it was back to pretreatment levels at around day 28. With regards to the calcium level, there was a sharp rise in this between days 2–4 but it was back to normal by day 7.

Discussion

Comparing the results for the different delivery systems clearly shows an enhanced and lasting inhibitory activity for vitamin $D_3$ in the lipiodol delivery system. This could be due to a number of factors including uptake retention and sustained release of vitamin $D_3$ from lipiodol. Previous reports (1, 2) employing different techniques, have shown the uptake of lipiodol by HCCs. Our results in this section, using HepG2 cell line and oil-red O impregnation technique clearly demonstrates the abundant uptake of lipiodol by these cells which is presumably brought about by endocytosis.

It has been shown that, the oil is retained within the cells as for the life of the cell (1). The prolonged intracellular retention of lipiodol appears to be a specific capability of hepatoma cells, as normal liver cells appear to take up and excrete it rapidly in a few days as compared to the very long retention of it by HCCs (2). Consequently, it may be hypothesized that the increased inhibitory activity observed during chronic treatment with vitamin D/lipiodol, might partly be due to the accumulation of lipiodol and hence vitamin $D_3$ within the cell. However, as can be seen from the results, this alone cannot account for the difference obtained between the two delivery systems. Another contributing factor might be the higher stability of vitamin $D_3$ in lipiodol as this may prevent extensive degradation and rapid exposure of the drug to the metabolizing enzymes (3). This can particularly be true in the present setting where vitamin $D_3$ is a drug which due to its chemical structure is vulnerable to extensive metabolism and to add to this, HepG2 is a cell line with extensive metabolizing capacities (4).

The data in the acute treatment experiments where a 24-h exposure of cells to a single dose of vitamin $D_3$/lipiodol results in significant inhibition of proliferation, may perhaps indicate the sustained release of vitamin $D_3$ from the intracellular lipiodol depots. This might well be the reason behind the differences observed in the greater and lasting inhibitory activity of vitamin D3 in lipiodol or MCT compared to that of vitamin $D_3$ in the medium alone. Results obtained in the Novikoff tumor bearing rats point put to the same point and confirm the validity of the cell culture studies in that vitamin $D_3$ in lipiodol and MCT, is taken up, retained and gradually released from the tumor HCC cells. However, as Novikoff is a vitamin $D_3$ resistant cell line, efficacy experiments could not be conducted in this model.

Although too early to comment, but results obtained in the one patient treated so far with the 50 μg dose of vitamin $D_3$/5 ml lipiodol is in line with the experimental data obtained in cell culture and rat studies. Plasma sample assay for vitamin $D_3$ levels (currently ongoing), should clearly show the behaviour of vitamin $D_3$/lipiodol in HCC.

In conclusion, the results presented above suggest that, vitamin $D_3$ dissolved in lipiodol produce an increased and sustained antiproliferative activity in the human HCC cell line HepG2 and is retained for considerably longer periods within the tumor as shown by the liver tumor experiments in the rat

References

1. Chou, F. I., Fang, K. C., Chung, C. et al. (1995) Lipiodol uptake and retention by human hepatoma cells. Nucl. Med, Biol. 22: 379–386.
2. Bhattacharya, S.; Dhillon, A. P., Winslet, B. R., et al. (1996) Human liver cancer cells and endothelial cells incorporate iodised oil, Br. J. Cancer 73: 877–881.
3. Prankerd R. J., Stella V. J. (1990) The use of oil-in-water emulsion as a vehicle for parenteral drug administration. J. Parenter. Sci. Technol, 44: 139–149.
4. Duthie, S. J., Melvin, W. T., Burke, M. D. (1995) Drug toxicity mechanisms in human hepatoma HepG2 cells: cyclosporin A and tamoxifen. Xenobiotica 25: 1151–1164.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A pharmaceutical composition suitable for use in the treatment of a tumor in an organ by regional delivery of the composition to the organ, wherein the composition consists essentially of a pharmaceutically acceptable lipid comprising a vitamin D compound and wherein the concentration of the vitamin D compound in the composition is greater than about $1 \times 10^{-7}$ mole per liter to less than $1 \times 10^{-3}$ mole per liter.

2. A composition according to claim 1, wherein the lipid is an oil.

3. A composition according to claim 1, wherein the oil is a non-iodised oil.

4. A composition according to claim 2, wherein the oil is poppy seed oil.

5. A composition according to claim 2, wherein the oil is an iodised oil.

6. A composition according to claim 2, wherein the oil is iodised poppy seed oil.

7. A composition according to claim 1, wherein the vitamin D compound is vitamin D or a precursor, metabolite or analogue thereof.

8. A composition according to claim 1, therein the concentration of the vitamin D compound in the composition is at least about $1 \times 10^{-6}$ mole per liter.

9. A composition according to claim 8, wherein the concentration of the Vitamin D compound is at least about $1 \times 10^{-5}$ mole per liter.

10. A composition according to claim 9, wherein the concentration of the vitamin D compound is at least $1 \times 10^{-4}$ mole per liter.

11. A composition according to claim 10, wherein the concentration of the vitamin D compound is at least $1 \times 10^{-3}$ mole per liter.

12. A composition according to claim 1, wherein the vitamin D compound is selected from the group vitamin $D_3$, 25(OH)$D_3$, 1,25(OH)$_2D_3$ and 24R, 25(OH)$_2D_3$ or a precursor, metabolite or analogue thereof.

13. A composition according to claim 1, wherein the vitamin D compound is selected from the group EB1089, 22-oxa-1,25(OH)$_2D_3$, 1α25(OH)$_2$, 22,24 diene, 24, 26, 27 trihomo $D_3$, calcipotriol and KH1060, 1,25(OH)$_2$-16-ene 23-yne vitamin $D_3$ and its hexadeutero form.

14. A composition according to claim 1 wherein the vitamin D compound is vitamin $D_5$ or an analogue or metabolite thereof.

15. A composition according to claim 1, wherein the oil is an oil for which the tumor is avid.

* * * * *